US006916423B2

(12) United States Patent
Bogoev et al.

(10) Patent No.: US 6,916,423 B2
(45) Date of Patent: Jul. 12, 2005

(54) DEVICE AND METHODS FOR SUBDIVIDING AND FILTERING GEL MATERIAL AND EXTRACTING MOLECULES THEREFROM

(75) Inventors: Roumen A. Bogoev, San Marcos, CA (US); Scott E. Whitney, San Diego, CA (US); Joseph W. Amshey, Encinitas, CA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/906,792

(22) Filed: Jul. 18, 2001

(65) Prior Publication Data

US 2002/0040872 A1 Apr. 11, 2002

Related U.S. Application Data (60) Provisional application No. 60/218,821, filed on Jul. 18, 2000.

(51) Int. Cl.[7] ........................... B01D 11/04; G01N 27/26
(52) U.S. Cl. ..................... 210/634; 204/456; 204/462; 210/650; 210/787; 241/1; 241/24.1; 436/178; 436/180
(58) Field of Search ................................. 210/232, 252, 210/257.1, 257.2, 266, 295, 314, 315, 323.2, 335, 337, 360.1, 321.72, 512.1, 513, 518, 634, 650, 781, 787; 204/456, 462; 241/1, 24.1, 25; 422/61, 72, 101, 102; 436/177, 180, 174, 178

(56) References Cited

U.S. PATENT DOCUMENTS

| 3,763,879 A | 9/1973 | Jaworek |
| 4,734,192 A | 3/1988 | Champion et al. |
| 4,948,561 A | 8/1990 | Hinckley et al. |
| 5,552,325 A * | 9/1996 | Nochumson et al. ....... 436/177 |
| 5,601,711 A | 2/1997 | Sklar et al. |

(Continued)

FOREIGN PATENT DOCUMENTS

WO    WO 99/39010    8/1999

OTHER PUBLICATIONS

Pluskal et al., "High Throughput In–Gel Peptide Digestion and Microscale Sample Preparation for MALDI–TOF MS Analysis", one (1) page, presented at Conference, May 14–17, 2001, Philadelphia, PA.

Retamal et al., "Protein Purification from Polyacrylamide Gels by Sonication Extraction", *Analytical Biochemistry* (1999) 268, pp. 15–20.

Ihara et al., "Recovery of Polypeptides from Polyacrylamide Gels by Electrophoretic Elution in a Centrifugation Concentrator", *Analytical Biochemistry* (1987) 166, pp. 349–352.

(Continued)

*Primary Examiner*—Joseph Drodge
(74) *Attorney, Agent, or Firm*—Sterne, Kessler, Goldstein & Fox P.L.L.C.

(57) ABSTRACT

An apparatus and method for mincing a gel includes a gel mincing tube and a mesh material. The mesh material extends across the end of the tube. To subdivide a gel using the mincing apparatus, a gel is placed upon the mesh material in the mincing tube, the mincing tube, mesh material and the gel are spun in a centrifuge, forcing the gel through the mesh material so that the gel is subdivided into generally uniform smaller fragments. The mesh material may be secured to a tube in the form of a nesting tube. The nesting tube nests within the opening of a recovery vessel. The mesh material may be placed in series with a conditionally porous membrane in the nesting tube. Centrifuging the nesting tube and the recovery vessel subdivides gel material into fragments by forcing the gel through the mesh material. The gel subsequently falls upon the membrane, and may be treated on the membrane to extract or otherwise treat analytes in the gel material.

19 Claims, 4 Drawing Sheets

U.S. PATENT DOCUMENTS

| | | |
|---|---|---|
| 5,833,860 A | 11/1998 | Kopaciewicz et al. |
| 5,853,586 A | 12/1998 | Valus et al. |
| 6,048,457 A | 4/2000 | Kopaciewicz et al. |
| 6,103,195 A | 8/2000 | Shukla et al. |
| 6,200,474 B1 | 3/2001 | Kopaciewicz et al. |
| 6,221,655 B1 | 4/2001 | Fung et al. |
| 6,291,249 B1 | 9/2001 | Mahant et al. |

OTHER PUBLICATIONS

Castellanos–Serra et al., "Fast Passive Elution of DNA from Zinc–Imidazole Negatively Stained Polyacrylamide Gels", *Analytical Biochemistry* (1998) 257, pp. 227–228.

Kobayashi et al., "Isolation of Enzymes from Polyacrylamide Disk Gels by a Centrifugal Homogenization Method", *Analytical Biochemistry* (1985) 145, pp. 351–353.

* cited by examiner

DEVICE AND METHODS FOR SUBDIVIDING AND FILTERING GEL MATERIAL AND EXTRACTING MOLECULES THEREFROM

CROSS-REFERENCE TO RELATED APPLICATION

This application claims the benefit of the filing date of U.S. Application No. 60/218,821, filed Jul. 18, 2000, the entire disclosure of which is incorporated herein by reference.

BACKGROUND OF THE INVENTION

Gel electrophoresis is a common procedure for the separation of biological molecules, such as deoxyribonucleic acid (DNA), ribonucleic acid (RNA), polypeptides and proteins. In gel electrophoresis, the molecules are separated into bands according to the rate at which an imposed electric field causes them to migrate through a filtering gel.

The basic apparatus used in this technique consists of a gel often enclosed in a glass tube or sandwiched as a slab between glass or plastic plates. The gel has an open molecular network structure, defining pores, which are saturated with an electrically conductive buffered solution of salts. These pores through the gel are large enough to admit passage of the migrating macromolecules.

The gel is placed in a chamber in contact with buffer solutions which make electrical contact between the gel and the cathode and anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known mobility, the mobility of other macromolecules can be determined. The size of the macromolecule can then be calculated or macromolecules of different sizes can be separated in the gel.

There are a wide range of gel-forming materials used for electrophoresis. Polyacrylamides, polymethacrylamides and other related polymers are preferred for separation of smaller molecular weight materials such as proteins, peptides and small nucleic acids. Conversely, agarose, cellulose acetate and starch are preferred for larger molecules. These gel materials are typically compatible with aqueous systems, though some are also compatible with non-aqueous solvents.

Formation of the gel material to the desired physical dimensions can be accomplished by varying techniques, depending on the material chosen. With agarose or gelatin the common method is to heat the polymer causing the material to go into solution. The solution can then be poured into a cast and allowed to polymerize by cooling. Alternatively, polyacrylamides, polymethacrylamides and other related polymers can be chemically polymerized by various means including free radical induced polymerization with ammonium persulfate and tetramethylethylenediamine.

A common problem with gel electrophoresis is the difficulty of removing the protein, nucleic acid or other analyte of interest from the gel after it has been separated from other components. Because the gel matrix has very small pore sizes, large molecules do not easily diffuse out of the gel matrix after they have been drawn into the matrix through electromotive force. Proteins also do not diffuse into the gel matrix readily in the absence of electromotive force. The larger the molecular weight of the protein the more difficult it is to get the molecules into or out of the gel. Thus, techniques have been developed for preparing a gel for extraction or introduction of molecules out of or into the gel.

The state of the art includes a procedure for gel subdivision using a sieve. Christoph Eckerskom and Rudolf Grimm describe the use of a stainless steel sieve placed in the end of a syringe barrel for subdividing gels. Eckerskorn and Grimm attribute their technique to J. Heukeshoven and R. Dernick, as described in B. Radola (ed.), *Electrophoresis Forum '91*, Technical University, Munich 1991, pp. 501–506. In another article, J. Lila Castellanos-Serra, et al., *Electrophoresis* 1999; 20: 732–737, a stainless steel sieve screen is used for subdividing gels to remove proteins for further analysis. This article attributes the idea to Eckerskorn and Grimm and to Heukeshoven and Dernick. Castellanos-Serra et al. placed a piece of stainless sieve screen in the narrow end of a syringe barrel and used the pressure of the plunger to force the gel through the screen.

However, this approach has significant disadvantages. First, the syringe is costly, especially if there are large numbers of gels to be processed simultaneously. This cost arises in part because the syringe comprises several parts including a barrel, plunger and gasket. Second, the user must manually force the gel through the mesh with the action of a plunger. This technique is significantly labor intensive and is not amenable to automation. Third, the plunger does not advance all of the gel cleanly through the mesh, because the force applied by the plunger stops at the top of the mesh.

Others have demonstrated that centrifugal force can be useful in forcing materials through a barrier for various purposes, e.g. a filtration membrane for separation. For example, U.S. Pat. No. 3,583,627 to Wilson describes concentrating a large molecular weight substance in solution by fixing a filter into the end of the upper of two nested tubes and spinning the tubes to force the solvent through the filter while retaining the macromolecules. There are numerous examples of using this basic principle to concentrate macromolecules, for example U.S. Pat. No. 4,632,761 Bower et al. These devices and methods, however, are designed for filtration of solutions and are not suitable for cutting or subdividing a semi-solid gel or other substance.

Additionally, Millipore Corporation of Bedford, Mass. currently sells Product No. 42600 "Ultrafree DA for DNA extraction," for the subdivision of gel fragments. This product also suffers from several drawbacks. First, it uses a nested tube set, the upper tube having in its base plastic projections molded in place that are supposed to subdivide a gel when the tube set is spun. However, in practice, these do not work well because the resulting subdivided gel has large, inconsistently-sized pieces of gel leading to inefficient and unreliable extraction. Second, the Millipore device is recommended primarily for agarose gels and may be used on polyacrylamide gels, but only with a maximum polymer concentration of 10% by weight. Gels having a polymer concentration less than 10% by weight are usually unable to efficiently separate very low molecular weight peptides and proteins, which often require 12%, 15%, 18% or a higher percentage of polymer concentration by weight.

There is, therefore, a need for a method of easily, efficiently, reliably and inexpensively subdividing a gel to facilitate the extraction of various molecules from the gel, or conversely, the introduction of molecules into the gel. In particular, as more and more analytes become available for study, e.g. through the Human Genome Project and followon projects to identify genes and express gene products, there is a need to perform such extractions or introductions in high-throughput and automated formats.

Although much of the description of the invention is related to removing proteins from gels, it is also often of interest to remove other molecules from gels. A person of ordinary skill in the art would readily apply the techniques described herein to other molecules commonly subjected to electrophoresis, e.g. nucleic acids such as DNA or RNA.

SUMMARY OF THE INVENTION

The present invention provides a convenient method of subdividing a gel containing a protein, nucleic acid or other analyte of interest into small, consistently-sized fragments, which facilitate the diffusion of reagents into, or analyte out of, the gel. In one embodiment, the apparatus of the present invention consists of a centrifuge tube incorporating a mesh or grid barrier, through which the gel is drawn by centrifugal force when the tube is spun, thereby forming a mincing tube. The mesh or grid is preferably one having small and consistent hole spacing within and between different manufacturing lots.

The mesh material extends across the end of the tube. To subdivide a gel using the mincing tube, a gel is placed upon the mesh material and the tube. When the mesh material and the gel are spun in a centrifuge, the gel is drawn through the mesh material so that the gel is subdivided into generally uniform smaller fragments.

The mesh material may be secured to a tube in the form of a nesting tube. The nesting tube nests within the opening of a recovery vessel. Alternatively, the mesh material may be placed in series with a conditionally porous membrane in the nesting tube. Centrifuging the nesting tube and the recovery vessel subdivides gel material into fragments by forcing the gel through the mesh material. The gel subsequently falls upon the membrane, and may be treated on the membrane to extract or otherwise treat analytes in the gel material.

In an alternate embodiment, the centrifuge tube may comprise parts or segments, with one part of the nested set including the mesh material to subdivide the gel. Another part provides a porous membrane or a conditionally porous membrane. Another part provides reversed phase capture material, either held in place by a membrane or by using membrane derived so as to bind proteins by hydrophobic interactions. Another part provides the immobilized antibody to capture a high abundance protein. Several types of such immobilized antibodies might be provided either as separate segments for nesting or combined in a single segment. The last segment can be a receptacle or recovery vessel for fluid driven through the column by centrifugal force.

A particular advantage of this invention is that it makes the process of subdividing the gel simple and suitable for automation. It is often the case that numerous samples must be processed for further analysis, such as determining their amino acid sequence. The device and method of the present invention avoids significant hands-on work, such as using a spatula to chop-up or crush a gel, prior to the extraction process.

One advantage of the present invention is that it significantly decreases the time required to elute a protein, or other analyte, from the gel or to get homogeneous distribution of a reagent being diffused into the gel. This advantage is achieved because the invention results in a very finely subdivided gel. Because the protein or other analyte must diffuse out of the gel matrix, the farther it must diffuse, the longer it takes to extract. Therefore, a very finely subdivided gel allows proteins, for example, to be quickly diffused into or out of a gel.

Further, the present invention results in consistent thickness of the gel fragments, which allows the diffusion distance for reagents going into the gel or diffusing out of the gel to be consistent. The time required for penetration of the fragments of subdivided gel by reagent, or diffusion of materials out of the fragments, will be consistent and reproducible only if the sizes of the fragments are consistent and reproducible. Gels subdivided manually will not have this consistency and therefore the amount of protein, for example, which diffuses out of the gel will be variable leading to inconsistent results in further characterization. Often, samples of gel contain only tiny quantities of protein to be used for subsequent characterization, so consistency and efficiency of elution from the gel matrix is very important.

Thus, the method and device of the present invention offer several advantages. First, the syringe described by Eckerskorn et al. is far more costly than a centrifuge tube. Second, centrifuging methods, as described in the present invention, are more readily and cheaply adaptable to automation than methods employing syringe/plunger-and-mesh devices. Third, the use of centrifugal force on the small gel fragments draws the fragments completely through the sieve and down into the collecting tube, thereby solving the problem in the prior art of gel material remaining in the syringe mesh after the motive force of pressure is removed. In contrast to the Millipore product (Product No. 46200) with its molded projections for subdividing the gel, the sieve approach of the present invention results in smaller and more consistent gel fragments resulting in more efficient and reliable analyte extraction. The present invention also, unlike the Millipore product, subdivides gel with polyacrylamide concentrations greater than 10%, because the centrifugal force effectively drives the gel through the sieving mesh material.

In additional specific embodiments, methods and apparatuses of the invention are used to subdivide gels having polyacrylamide concentrations ranging from about 3% to 10%, about 5% to 10%, about 10% to 11%, about 10% to 12%, about 10% to 15%, about 10% to 18%, about 10% to 20%, about 12% to 15%, about 12% to 18%, about 12% to 20%, about 15% to 18%, about 15% to 20% and about 18% to 20%. Likewise, in other specific embodiments, the invention subdivides any other gel types, including, but not limited to, agarose gels.

In one aspect of the invention, a method for subdividing a semisolid material using a mincing tube having a mesh material disposed therein, comprises the steps of: placing the semisolid material upon the mesh material of the mincing tube; and centrifuging the mincing tube, the mesh, and the semisolid material to facilitate passage of the semisolid material through the mesh, thereby subdividing the semisolid material into fragments. Further steps may comprise: introducing an extraction solution into the mincing tube to extract an analyte from the semisolid material; incubating the mincing tube including the extraction solution and the semisolid material; and eluting the analyte from the subdivided semisolid material, wherein the extracted analyte may be a macromolecule, or alternatively, at least one or more of: proteins, peptides, nucleic acids and carbohydrates. Furthermore, the mesh material may span a lumen of the mincing tube, and the mesh material may be concave from a top edge of the mincing tube.

Further steps may include introducing an extraction solution into the mincing tube to extract analytes from the semisolid material, wherein the extraction solution and the analytes create an analyte solution; and transferring the analyte solution into a recovery vessel, the recovery vessel having a conditionally porous material disposed therein, such that the analyte solution may be in contact with the conditionally porous material. Additionally, the method may include centrifuging the recovery vessel with the analyte solution, such that some or all of the analyte solution flows through the conditionally porous material, wherein the conditionally porous material comprises one or more components selected from the group consisting of a long-chain alkyl group, an ion exchange group, a short chain carboxylate or sulfonate, an affinity group (e.g., an antibody), streptavidin, a chelating group or a boronic acid. In one aspect of the method, the conditionally porous material may be a polyvinylidene difluoride membrane a nylon membrane, a nitrocellulose membrane and/or a glass fiber membrane and the semisolid material may be an electrophoresis gel, or a subportion thereof.

In another aspect of the invention, a method for the treatment of a semisolid material using a first treating tube having a conditionally porous material disposed therein, comprises the steps of: combining the semisolid material with reactants in the first treating tube to create a reaction mixture; and centrifuging the first treating tube, such that some or all of the reaction mixture may be drawn through the conditionally porous material. The method may further comprise placing the first treating tube in a recovery vessel, such that the first treating tube may be nested into the recovery vessel; and capturing the reaction mixture in the recovery vessel. Alternatively, the method may further comprise: providing a second treating tube for nesting with the recovery vessel, wherein the second treating tube includes a second conditionally porous material; nesting the first treating tube in the second treating tube and nesting the second treating tube in the recovery vessel; centrifuging the first and the second treating tubes; and capturing the reaction mixture in the recovery vessel. The conditionally porous material may be a polyvinylidene difluoride membrane, a nylon membrane, a nitrocellulose and/or a glass fiber membrane and, in one aspect of the method, the first treating tube may be an array of treating tubes for aligning and mating with a microtiter plate. The first treating tube may include a mesh material at a first end of a lumen of the first treating tube, and the conditionally porous material may be disposed at a second end of the lumen of the first treating tube. The reactants may be disposed on the conditionally porous material, and the reactants may comprise one or more components selected from the groups consisting of a long-chain alkyl group, an ion exchange group, a short chain carboxylate or sulfonate, an affinity group (e.g., an antibody), streptavidin, a chelating group or a boronic acid. Furthermore, the semisolid material may be an electrophoresis gel, or a subportion thereof.

Another aspect of the invention includes a method for the division of a semisolid material using a mincing tube having a mesh material disposed therein, wherein the mincing tube may be nested in a recovery vessel such that substances passing through the mesh material are captured in the recovery vessel, the method comprising the steps of: placing a semisolid material in the mincing tube; and centrifuging the mincing tube and the recovery vessel until the semisolid material is divided into fragments by the mesh material. The method may further comprise the step of: providing a treating tube nested in series after the mincing tube and before the recovery vessel, wherein the treating tube includes a conditionally porous material disposed therein, and the conditionally porous material is in series with the mesh material. Further, the conditionally porous material may comprise one or more of the group consisting of: a long-chain alkyl group, an ion exchange group, a short chain carboxylate or sulfonate, an affinity group (e.g., an antibody), streptavidin, a chelating group or a boronic acid.

An apparatus for the subdivision of semisolid materials, may comprise: a mincing tube; and a mesh disposed in the mincing tube, wherein when the mincing tube is subjected to centrifugal forces, a semisolid material placed within the mincing tube on one side of the mesh is drawn through the mesh. The semisolid material may be an electrophoresis gel, or a subportion thereof, and may contain a protein or nucleic acid. Furthermore, the gel may have a polyacrylamide concentration greater than 10 percent or less than 10 percent. The mesh of the apparatus may be a metal or a polymeric mesh, such as a stainless steel mesh or a nylon mesh. The mesh may have a hole size ranging from 0.01 mm$^2$ to 9 mm$^2$, and the size of holes in the mesh may be substantially uniform. The mesh may cover an end of the mincing tube, and may be flat or formed to extend concavely into the mincing tube. The mesh may be fixed to the mincing tube by welding, by an adhesive, or by a compression ring.

The apparatus may be in a kit including a buffered solution (which may or may not comprise one or more extraction reagents such as one or more enzymes or the like), printed instructions for use of the apparatus, a spare mesh material, particles treated with, or having affixed thereto, an immobilized antibody, and a treating tube containing a conditionally porous mesh material disposed therein.

Another embodiment of the apparatus for the recovery of proteins and nucleic acids from a gel comprises: a mincing tube having a lumen, the mincing tube including a first conditionally porous material extending across the lumen and a mesh material extending across the lumen; and a recovery vessel disposed adjacent to the mincing tube, such that contents of the mincing tube flow through the mesh material and the conditionally porous material into the recovery vessel. The mincing tube may be nested within the recovery vessel. Additionally, the apparatus may include a treating tube containing a second conditionally porous material, wherein the treating tube is disposed adjacent the mincing tube so that the contents flow through the mesh material, the first conditionally porous material and the second conditionally porous material in series. The mincing tube may be nested within the treating tube, and the treating tube may be nested within the recovery vessel. In one aspect of the invention, the mincing tube and the treating tube are arrays of tubes that align with and mate with a microtiter plate. Contents of the apparatus may include an extraction buffer and proteins. Further, the first conditionally porous material may contain one or more of immobilized enzymes (e.g., proteases such as trypsin, chymotrypsin, pepsin, papain and the like), immobilized carbon chains and immobilized antibodies. The first conditionally porous material may be a polyvinylidene difluoride membrane, a nylon membrane, a nitrocellulose membrane and/or a glass fiber membrane. In one aspect, the mincing tube may comprise: a first portion containing the mesh; and a second portion containing the first conditionally porous material, such that the contents of the mincing tube flow through the mesh and the first conditionally porous material in series. The first portion may be nested with the second portion and the second portion may be nested with the recovery vessel. The first and the second portions may be arrays of tubes for aligning with and mating with a microtiter plate. The mesh material may be a metal or fabric mesh, wherein the mesh is a stainless steel mesh or a nylon mesh having a hole size ranging from 0.01 mm$^2$ to 9 mm$^2$.

Another embodiment of an apparatus for subdividing and processing a gel comprises: a mincing tube having a mesh material disposed therein; and a recovery vessel connected to the mincing tube, wherein a conditionally porous material is disposed within the recovery vessel. A reagent may be attached to the conditionally porous material, and the reagent may be one of immobilized trypsin, immobilized carbon chains and immobilized antibodies. The recovery vessel may be removably connected with the mincing tube in an inverted relationship. The mesh may a metal or fabric mesh, such as a stainless steel mesh or a nylon mesh having a hole size ranging from 0.01 mm$^2$ to 9 mm$^2$. The conditionally porous material may be a polyvinylidene difluoride membrane, a nylon membrane, a nitrocellulose membrane and/or a glass fiber membrane.

BRIEF DESCRIPTION OF THE FIGURES

The foregoing and other features and advantages of the invention will be apparent from the following, more particular description of preferred embodiments of the invention, as illustrated in the accompanying drawings.

DETAILED DESCRIPTION OF THE INVENTION

Preferred embodiments of the present invention are now described with reference to the figures where like reference numbers indicate identical or functionally similar elements. A person skilled in the relevant art will recognize that other configurations and arrangements can be used without departing from the spirit and scope of the invention. Furthermore, although the invention is described with reference to subdividing and treating electrophoresis gels, or subportions thereof, the invention is further applicable to any semisolid material, with the only limitation on the material being that it is subdividable through a mesh or screen material. Additionally, although the description of the invention primarily describes the invention as recovering proteins from the gels, the present invention can be used to recover other substances, including, but not limited to, nucleic acids, peptides, oligonucleotides and carbohydrates, and combinations thereof (e.g., glycoprotein, proteoglycans, nucleic acids, peptide-nucleic acid complexes and the like). Alternatively, the invention can be used to recover any macromolecule.

As used herein, the term "macromolecule" refers to polymeric and non-polymeric molecules which are larger than a specified size (see below) or contain more than a specified number of monomeric units (see below). Non-polymeric macromolecules will typically have a molecular weight over about 10,000 daltons. Further, polymeric macromolecules, such as proteins, will typically comprise more than 25 amino acids. Polymeric macromolecules, such as nucleic acids, will typically comprise more than 40 nucleotides. Polymeric macromolecules, such as multimeric carbohydrates, will typically comprise more than 10 individual sugar monomers. Polymeric macromolecules, other than those described above, would be apparent to one skilled in the art and may include combinations of the polymeric molecules described above (e.g., peptide-nucleic acids). The term "macromolecule" does not include molecules of the particular gel (e.g., agarose, polyacrylamide, etc.) from which analytes are extracted.

As used herein, the term "peptide" refers to polymers composed of 25 or fewer amino acids.

As used herein, the term "oligonucleotide" refers to polymers composed of 40 or fewer nucleotides.

As used herein, the term "purified," when applied to a particular molecule, means that the molecule is separated from at least some surrounding contaminants. Contaminants include molecules which are normally associated with the molecule which is purified. For example, an intracellular protein is purified when it is separated from at least some nucleic acid and protein molecules which normally co-reside with it in a cell. As one skilled in the art would recognize, the term "purified" is relative and, in essence, means that the concentration of a molecule, with respect to other molecules with which it is normally associated, is increased. For example, passage of a protein mixture over a molecular weight column may result in dilution of a particular protein (i.e., the protein which is being purified) and an increase in the concentration of this protein with respect to other protein present in the original mixture. Thus, generally, the term purified does not mean that the molecule subjected to processes which lead to purification is separated from reagents such as buffers or compounds such as water.

As used herein, the term "isolated," when applied to a particular molecule, means that the molecule is separated from substantially all of the surrounding contaminants. Thus, the term "isolated" means that molecule being isolated is at least 95% pure, with respect to the amount of contaminants originally present. In other words, the molecule which is isolated is separated from at least 95% of the surrounding contaminants.

The present invention uses a sieving screen to subdivide the gel in an inexpensive format that lends itself to automation. Screens of metal mesh material or fabric mesh material can be used to subdivide the gel into uniformly small fragments. The screens may have openings that range from 0.01 mm$^2$ to 9 mm$^2$. Preferably, the openings each have an area from 0.09 mm$^2$ to 0.36 mm$^2$. The openings may be any shape, including square, rectangular, oval, circular, triangular or any variation thereof. Regardless of the shape of the openings, the area of the openings, in specific embodiments ranges from about 0.01 mm$^2$ to mm$^2$ to 0.1 mm$^2$, about 0.01 mm$^2$ to 1 mm$^2$, about 0.01 mm$^2$ to 2 mm$^2$, about 0.01 mm$^2$ to 9 mm$^2$, about 0.01 mm$^2$ to 5 mm$^2$, about 0.1 mm$^2$ to 1 mm$^2$, about 0.1 mm$^2$ to 5 mm$^2$, about 0.1 mm$^2$ to 9 mm$^2$, about 1 mm$^2$ to 5 mm$^2$, about 1 mm$^2$ to 9 mm$^2$ and about 5 mm$^2$ to 9 mm$^2$.

Screens such as metal sieve, used to separate particles by their size, and fabrics such as nylon mesh are commercially available with openings from less than 0.09 mm$^2$ to 0.36 mm$^2$ or larger, and are highly consistent across multiple lots of product. These screens and fabrics are available from numerous vendors, including, but not limited to, McMaster-Carr, Santa Fe Springs, Calif. 90670-2932. Such materials may be largely inert when made of appropriate materials such as stainless steel or nylon. When the gel is mechanically forced through these materials, it breaks into very small fragments with consistent thickness, (J. Lila Castellanos-Serra, et al., *Electrophoresis* 1999; 20: 732–737).

The device can be used to capture intact protein by elution from the gel fragments produced by centrifugation through the mesh material. Conventionally, proteins are removed from gels by electroelution, a method of passing a current through the gels to remove them by the same mechanism which caused them to separate in the gels originally. See Hunkapiller, M. W., et al., in *Methods in Enzymology*, C. H. W. Hirs and S. N. Timasheff eds., Academic Press, New York, Vol. 91, p. 227. However, when the gel is subdivided into very small elements, a significant portion of the protein can be eluted directly. Protein eluted in this way can be sequenced using automated sequencers such as are available from Beckman Instruments or Applera, Inc. among others.

Figure 1:
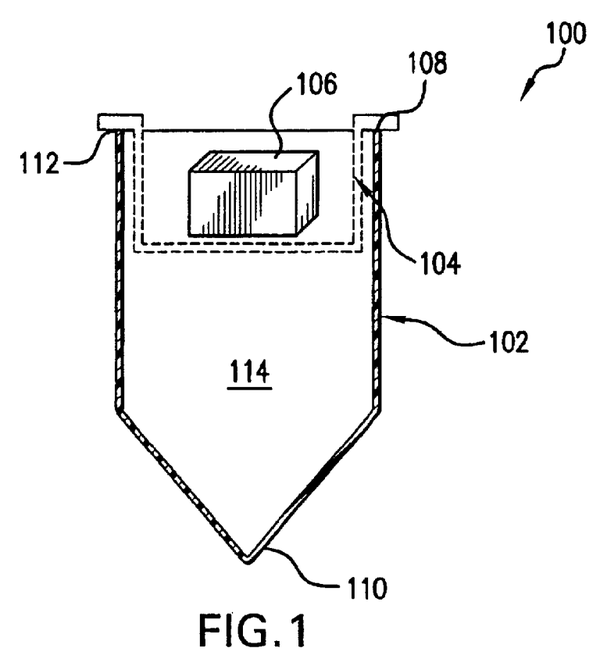
FIG. 1 shows a gel mincing tube including a mesh material.

FIG. 1 shows an embodiment of gel mincing apparatus for dividing a gel into subdivided fragments. Apparatus 100 includes a gel mincing tube 102 and a screen or mesh material 104. Mincing tube 102 can be a plastic centrifuge tube, as is shown in FIG. 1. Mincing tube 102 has an open end 108 and a closed end 110, forming an interior cavity 114. Mincing tube 102 could be a bowl, a dish, a bucket or any vessel having an open end and a closed end, thereby being capable of containing a fluid. As is explained with respect to alternate embodiments below, the mincing tube may include two open ends, with a lumen extending therebetween. In the embodiment shown, mincing tube 102 is similar in shape to an Eppendorff centrifuge tube, such that closed end 110 is in a cone shape.

Mesh material 104 extends across open end 108 of mincing tube 102. Mesh material 104 may be perpendicular to a longitudinal axis of mincing tube 102, or may have a concave shape extending from a tube edge 112 into cavity 114, as is shown in FIG. 1. Mesh material 104 may removably rest upon tube edge 112, or, alternatively, may be fixed to tube edge 112. Mesh material 104 should be secured to mincing tube 102 in such a way that during centrifuging, the forces imposed on mesh material 104 do not advance the mesh further into cavity 114 toward closed end 110.

To subdivide a gel using mincing apparatus 100, a gel 106 is placed upon mesh material 104 above cavity 114. Gel 106 could be any gel, but preferably is a electrophoresis gel or a subportion thereof. Mincing tube 102, mesh material 104 and gel 106 are spun in a centrifuge, forcing gel 106 consistently through mesh material 104 so that the gel is subdivided into smaller fragments. Mesh material 104 can be secured into open end 108 of mincing tube 102, so that when gel 106 is placed on mesh material 104, the tube can be placed into the centrifuge without spilling the gel.

Mesh material 104 can be inserted into mincing tube 102 so that it is held in place by mechanical forces. Specifically, a piece of stainless steel mesh material can be cut to be about twice the diameter of the top of the mincing tube. The portion of the mesh above the opening of the mincing tube is pressed into the mincing tube so that the mesh is somewhat concave, and extends into the opening. The edges of mesh 104 that extend outside of the mouth of mincing tube 102 can be bent over to hold the mesh in place. Gel sample 106 to be subdivided is placed in the concavity above mincing tube cavity 114 and the entire assembly is centrifuged. Alternative methods for holding the mesh in place include, but are not limited to, gluing, welding or otherwise fixing the mesh to the top of the mincing tube so that it hangs into the mincing tube cavity. Fixing the mesh to the top of the mincing tube is useful when using a flexible mesh, such as a nylon mesh. The mincing tube may be made from a centrifuge tube available from Millipore Corporation (Bedford, Mass.), Brinkmann (Westbury, N.Y.), Fisher Scientific (Pittsburgh, Pa.) and others, as described below.

In lieu of mincing tube 108, a microtiter plate could be used, having a mesh material disposed therein. Such use of a microtiter plate allows high throughput and efficient subdividing of a plurality of gel pieces.

Figure 2:
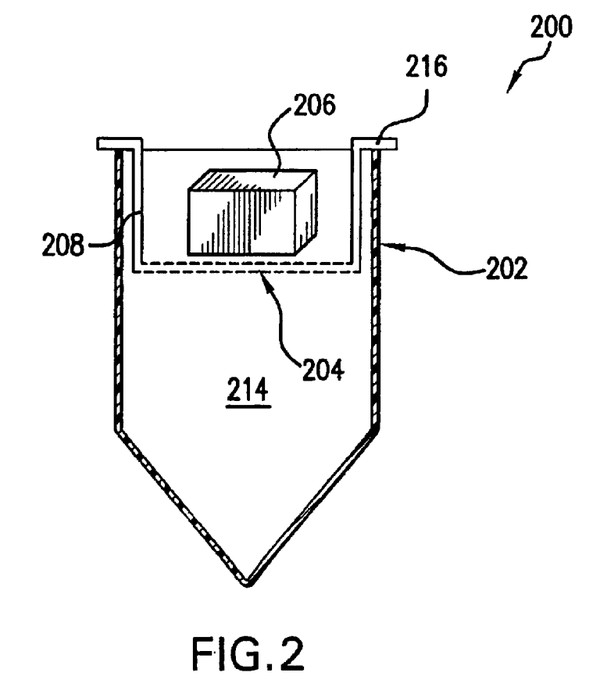
FIG. 2 shows a nested gel mincing tube including a mesh material.

FIG. 2 shows an alternate embodiment of a gel mincing apparatus 200. In this embodiment, a mesh material 204 is secured to a base of a nesting mincing tube 208. Mesh material 204 could be secured to nesting mincing tube 208 by an adhesive, by a weld, tied around nesting mincing tube 208, by a compression ring or attached by any other means known in the relevant art. Alternatively, mincing tube 208 could have a step formed into the tube lumen, and mesh material 204 could be lodged across the lumen, on the step.

Nesting mincing tube 208 has an outer diameter smaller than the inner diameter of a recovery vessel 202, and is removably placed within a cavity 214 of recovery vessel 202. In a preferred embodiment, recovery vessel 202 is a centrifuge tube similar to mincing tube 102 described above with reference to FIG. 1. A lip 216 is located around an upper end of nesting mincing tube 208, and radially extends from the upper end of nesting mincing tube 208 to a diameter greater than the inner diameter of recovery vessel 202. Accordingly, lip 216 secures nesting mincing tube 208 into recovery vessel 202, limits the distance that nesting mincing tube 208 can extend into cavity 214 during centrifuging, and serves as a convenient gripping point when removing nesting mincing tube 208 from recovery vessel 202. Nesting mincing tube 208 and recovery vessel 202 are preferably formed of an inert plastic material. However, as would be apparent to one skilled in the relevant art, nested tube 208 and recovery vessel 202 could be formed of any plastic, metal or other material.

Nesting mincing tube 208 is conveniently nested within recovery vessel 202 during use. Likewise, when desired, a user could remove nesting mincing tube 208 from recovery vessel 202 to further aid in processing of a gel sample, as will be explained below. Although nesting mincing tube 208 is shown having mesh material 204 located at an end of the nesting tube, mesh material 204 could be secured within nesting mincing tube 208 in a middle region or at the opposite end of that shown in FIG. 2. Preferably, mesh material 204 is located at the lower end, as shown, or somewhere in the middle region so that a gel 206 can be easily placed upon mesh material 204 without spilling.

Nested tubes, as disclosed in FIG. 2, could be created by modifying a standard centrifuge nesting tube set used for concentration or ultrafiltration made by, for example, Millipore Corporation and others. One method of creating the nested tube set is to cut off a bottom of a standard nesting tube in the region of the ultrafiltration membrane, and to attach a mesh material by gluing or by melting the nesting tube plastic so as to weld the mesh material to the nesting tube. The nesting tube may then be placed into the centrifuge tube of the standard nesting tube set, the gel sample may be placed atop the mesh in the nesting tube and the nested pair may be spun in a centrifuge. The subdivided gel fragments then collect in the centrifuge tube where the fragments may be subjected to further processing.

Figure 3A:
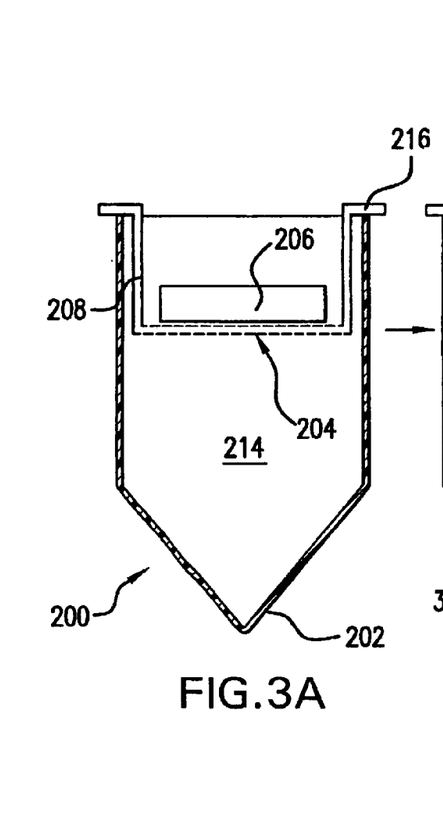
FIGS. 3A–3D show the use of the nested tube of FIG. 2, including processing of the sub-divided gel and a basic recovery technique.
Figures 3B, 3C:
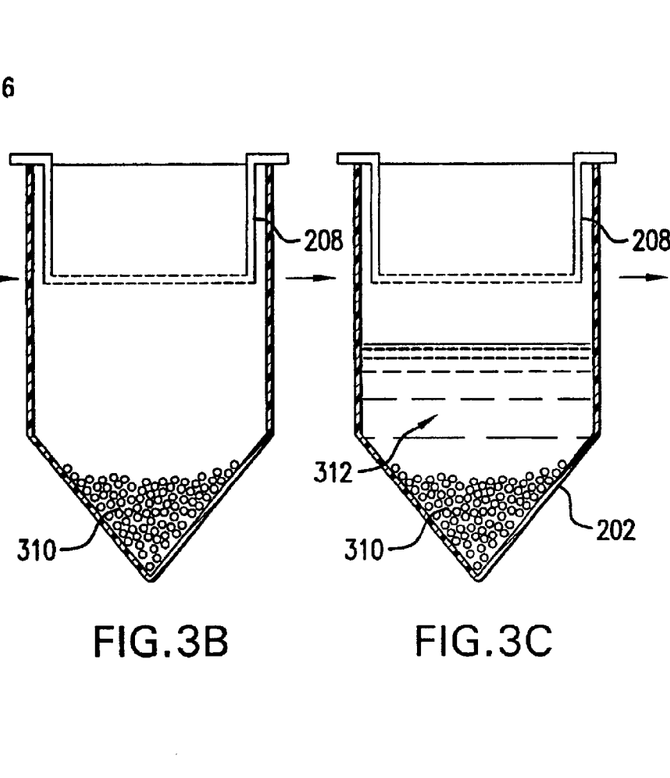

FIGS. 3A–3D show a process for extracting samples from a gel using the gel mincing apparatus of FIG. 2. FIG. 3A shows the gel mincing apparatus 200 of FIG. 2, including nesting mincing tube 208, mesh material 204 and recovery vessel 202. In use, a gel 206 is placed within nesting mincing tube 208 of mincing apparatus 200. Apparatus 200 is centrifuged until gel 206 is drawn by centrifugal force through mesh material 204 into cavity 214. As gel 206 is drawn through mesh material 204, gel 206 is subdivided into a plurality of substantially similarly sized subdivided fragments 310, as shown in FIG. 3B.

Following the subdivision of the gel by centrifugation through the mesh, an extraction buffer solution 312 may be introduced into recovery vessel 202, as is shown in FIG. 3C. Although the invention is described with use of an extraction buffer solution, the solution need not be a buffer solution, but could be any extraction solution. Accordingly, extraction buffer solution 312 may or may not include a buffer. Extraction buffer solution 312 may be poured through the lumen of nesting mincing tube 208 and through mesh material 204 into recovery vessel 202. Commonly, extraction buffer solutions are prepared with volatile salts, such as ammonium bicarbonate, which facilitates subsequent freeze drying. However, any standard extraction solvent may be used, as would be apparent to one skilled in the relevant art. After introducing extraction buffer solution 312, the subdivided gel sample may be incubated. The technical specifications for incubation times and temperatures are known or determined experimentally, as elution efficiency is dependent on the molecular weight of the analyte, the amount of polymer per unit weight of gel and the size of the gel fragments.

Figure 3D:
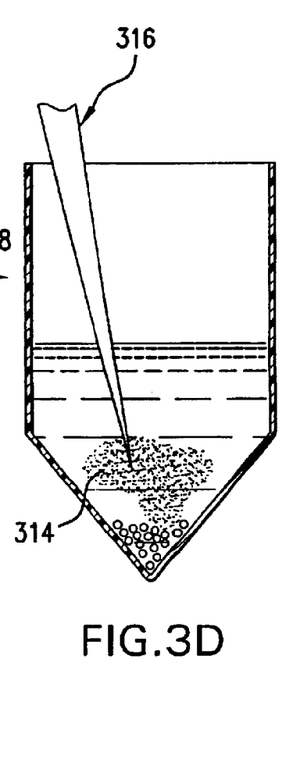

During incubation, extraction buffer 312 elutes analytes, such as proteins, from gel subdivided fragments 310, creating a buffer-analyte solution 314 as shown in FIG. 3D. Buffer-analyte solution 314 may also include any analyte that is commonly subjected to electrophoresis, including, for instance, proteins and nucleic acids, such as DNA and RNA. After incubation, nesting mincing tube 208 may be removed from recovery vessel 202, and a pipette 316 may be used to obtain the eluted sample. Although nesting mincing tube 208 was removed from recovery vessel 202 after incubation, it would be equally obvious to remove nesting mincing tube 208 prior to incubation or prior to introducing extraction buffer solution 312 to recovery vessel 202.

Proteins eluted from the gel fragments may be used for further analysis. For example, proteins are frequently examined for their tendency to bind to other proteins indicating possible interactions that may take place between these proteins within the cell. Methods for evaluating such interactions include equilibrium dialysis, surface plasmon resonance changes, and others. Moreover, such eluted proteins may be used to evaluate interactions with small molecules such as intracellular messenger compounds or potential drug substances. If an eluted protein is important in the regulation of cellular function, it is frequently desirable to determine whether its function can be modulated with small molecules that are potential drug substances.

FIGS. 4A–4D show an alternative embodiment of a gel mincing apparatus 400, including an alternative method of recovery by inverting the mincing tube into a recovery vessel. A gel mincing tube 402 includes an open end 407 and a closed end 408. Similar to the embodiments of FIGS. 1 and 2, a mesh material 404 is disposed within mincing tube 402, spanning the diameter of mincing tube 402. In this embodiment, mesh material 404 is shown spanning the diameter in a central region of mincing tube 402. As would be apparent to one skilled in the relevant art, mesh material 404 could be located at or near open end 407 or near closed end 408 of mincing tube 402.

Figure 4A:
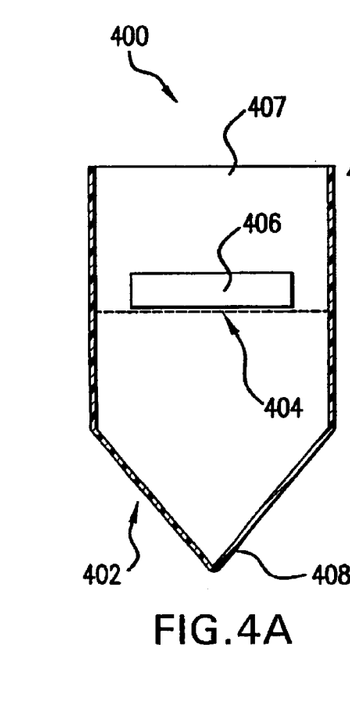
FIGS. 4A–4D show the use of an alternative embodiment of a gel mincing tube, including an alternative method of recovery by inversion of the gel mincing tube into a recovery vessel.
Figure 4B:
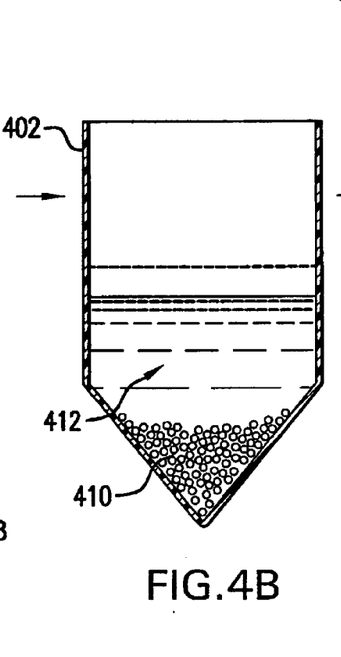
Figure 4C:
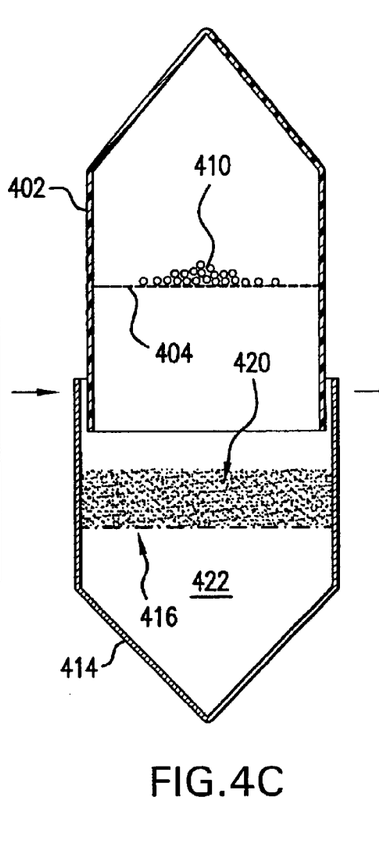

A gel 406 is placed within mincing tube 402 on mesh material 404, as is shown in FIG. 4A Mincing tube 402, mesh material 404 and gel 406 are centrifuged until gel 406 passes through mesh material 404, and is thereby subdivided into gel fragments 410 as is shown in FIG. 4B. An extraction solution 412 is introduced into mincing tube 402, as is shown in FIG. 4B. As would be apparent to one skilled in the relevant art, extraction solution 412 could be a buffer solution. Mincing tube 402 is incubated with extraction solution 412 and gel fragments 410 to draw analytes out of the gel fragments, thereby creating an analyte solution 420. After incubation, analyte solution 420 is poured from recovery vessel 202 into a recovery vessel 414. As can be seen in FIG. 4C, the remaining gel fragments are restrained within mincing tube 402 by mesh material 404.

Recovery vessel 414 may optionally include a membrane 416 of polyvinylidene difluoride, nylon, nitrocellulose, glass fiber or other porous material, disposed within a cavity 422. Recovery vessel 414 preferably has an inner diameter greater than the outer diameter of mincing tube 402 so that mincing tube 402 may be inverted and placed within recovery vessel 414 to reduce spilling and to allow the analyte solution to completely drip into recovery vessel 414, as is shown in FIG. 4C. However, as would be apparent to one skilled in the relevant art, the diameters of mincing tube 402 and recovery tube 414 could be the same, or the diameter of mincing tube 402 could be smaller or larger than the diameter of recovery vessel 414. Membrane 416 spans the diameter of cavity 422.

Mincing tube 402 may attach to recovery vessel 414 using any standard technique. For example, mincing tube 402 may have a peripheral lip (not shown), extending from a circumference of mincing tube 402 from an area located between open end 407 and closed end 408. Thus, the lip allows mincing tube 402 to rest inverted on recovery vessel 414. Likewise, mincing tube 402 could be friction fit into the inner diameter of recovery vessel 414, thereby securing mincing tube 402 in an inverted position. In an alternative embodiment, mincing tube 402 could be taped, clipped or include threads that allow mincing tube 402 to be secured or threaded onto recovery vessel 414.

When poured into recovery vessel 414, analyte solution 420 occupies the area above membrane 416. Membrane 416 is a conditionally porous material, meaning that the pores of the membrane are small enough to restrict passage of a solution through the membrane except when a force is applied to the solution. Accordingly, as is seen in FIG. 4C, analyte solution 420 is contained in the area above membrane 416.

Figure 4D:
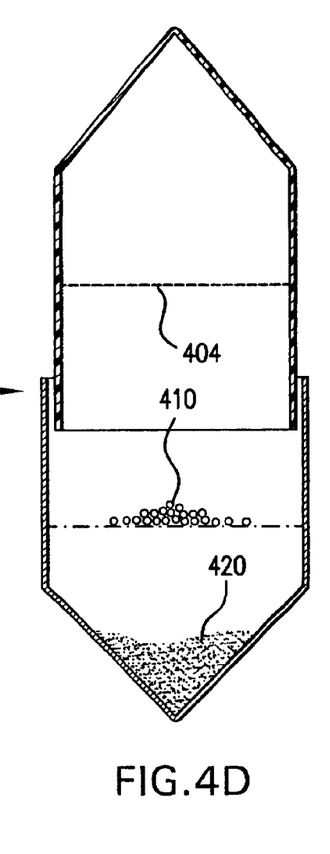

To filter and recover the analytes from analyte solution 420, recovery vessel 414 and mincing tube 402 are centrifuged. During centrifuging, analyte solution 420 is drawn through the pores of membrane 416 into cavity 422. Gel fragments 410 are again drawn through mesh material 404, and fall onto membrane 416 as shown in FIG. 4D. The centrifugation allows for complete recovery of the eluted product and, simultaneously, membrane 416 separates gel fragments 410 from the eluted product making the recovery more pure.

In one embodiment, membrane 416 is a Biodyne C membrane from Pall Gelman Corp. of Ann Arbor, Mich. A Biodyne C membrane is a nylon 6,6 membrane with pore surfaces populated by a high density of carboxyl groups. The Biodyne C membrane may be modified to create a reverse phase surface. One way of modifying the membrane is to incubate a 7 cm×7 cm membrane in 50 mL of 100 mM MES (morpholinoethane sulfonic acid) pH 5.5 containing 20 mM EDC (1-(3-dimethylaminopropyl)-3-ethylcarbodiimide hydrochloride) for 15 minutes at room temperature in a polypropylene container on a rotary shaker. After incubating, 5 mL of 0.5 M N-hydrosuccinimide in water (or sulfo-N-hydroxysuccinimide) is added and mixed thoroughly for 20 minutes. The solution in decanted and the membrane is washed with fresh MES buffer. The membrane is then incubated with 50 mM hexadecyl amine in 0.1 M $NaHCO_3$ pH 8.1 containing 50% tetrahydrofuran. The membrane is incubated for 2 hours at room temperature with shaking, and then the membrane is washed for 3 successive washes with 0.1 $NaHCO_3$ for 10 minutes, followed by three 10 minute water washes. The membrane is allowed to air dry. The Biodyne C membrane may be used by itself as a cation exchange resin.

The Biodyne B membrane, also manufactured and sold by Pall Gelman Corp., can be used as a strong anion exhange membrane for capture of peptides or proteins. The Biodyne B membrane is a good capture membrane for oligo nucleotides.

As would be apparent to one skilled in the relevant art, mincing tube 402 need not be centrifuged while inverted above recovery vessel 414. However, such joint centrifuging is desirable because it aids in transferring all of the analyte solution from mincing tube 402 to recovery vessel 414. Thus, this method allows treating and processing without requiring that the mesh material be removed.

Protein eluted from gel fragments 410 may be captured by membrane 416. Membrane 416 could be a polyvinylidene difluoride membrane such as the Invitrolon P, available from Invitrogen Corp., Carlsbad, Calif., or other materials having affinity for protein including those materials described elsewhere herein.

In an alternate embodiment, the membrane is placed in a nested tube set such that the protein is spun through the membrane to effect capture, as will be described below with reference to FIG. 5. Captured proteins may be sequenced using the Edman method on automated sequencers. See K. J. Wilson and P. M. Yuan, "Peptide and Protein Purification", in *Protein Sequencing: A Practical Approach*, J. B. C. Findlay and M. J. Geisow, eds., IRL Press, Oxford, 1989, p. 1. Protein eluted from the subdivided gel fragments is captured on the membrane and the membrane can be cut out and placed directly in the automated sequencer device.

In other embodiments of the present invention, additional features can be designed into the centrifugal gel mincing apparatus to accomplish other preparation steps on the extracted analyte. In particular, additional sample processing steps can be conducted in the same or in nested sets of tubes. Such processing is particularly desirable because once the gel fragments are subdivided, they more readily lend themselves to treatments with solvents and other reagents. This is due to the fact that the smaller gel fragments allow the molecules (analytes) embedded in them to more easily and quickly contact or diffuse into such reagents.

For example, proteins isolated in gel slices are commonly treated with trypsin or other oft-known proteolytic enzymes (collectively referred to as proteases) to cleave them into peptides for further analysis. See T. Rabilloud, et al., *Electrophoresis* 1999; 20, 3603-3610. Segments of the gel containing protein, visualized as spots by use of protein stains, are excised, chopped and dehydrated by air-drying or by using water miscible volatile solvents such as acetonitrile. They are then rehydrated in buffer containing trypsin or other proteases and digested for 15 hours at 37° C. The peptides formed by the digestion of the proteins are then extracted with mixed solvents.

The methods of the invention could be performed by proteases digestion times of greater or less than 15 hours (e.g., about 30 minutes, about 1 hour, about 2 hours, about 5 hours, about 10 hours, about 20 hours, etc.), such as a range of time from about 7 hours to 20 hours, 9 hours to 20 hours, 12 hours to 20 hours, 14 hours to 20 hours, 16 hours to 20 hours, 9 hours to 16 hours, 12 hours to 16 hours, 14 hours to 16 hours, 9 hours to 14 hours, 12 hours to 14 hours and 9 hours to 12 hours. Likewise, proteases digestion temperatures could range from about 25° C. to 45° C. (e.g., about 25° C., about 30° C., about 35° C., about 37° C., about 40° C. deg, etc.), about 30° C. to 45° C., about 32° C. to 43° C., about 32° C. to 40° C., about 32° C. to 37° C., about 32° C. to 34° C., about 34° C. to 42° C., about 34° C. to 37° C. and about 37° C. to 40° C.

Trypsin, as well as other proteins, can be immobilized onto a membrane, polymer or solid support such as glass particles using a variety of common techniques. W. V. Bienvenut, et al., *Analytical Chemistry* 1999; 71(21), 4800–4807 describes the immobilization of trypsin onto a chemically modified polyvinylidene difluoride membrane containing activated carboxylic acid groups. The protein amino groups react with the activated carboxylic acids linking the protein to the membrane. Many other immobilization techniques are also well known in the art and are well described in *Chemistry of Protein Conjugation and Cross-Linking*, by Shan S. Wong, CRC Press, New York, 1993. The immobilized trypsin, or any other protease, can then be placed in a layer beneath the subdivided gel, such that the proteins eluted from the gel will interact with the layer thus being cleaved into peptides without contaminating the sample itself with free trypsin.

Figure 5:
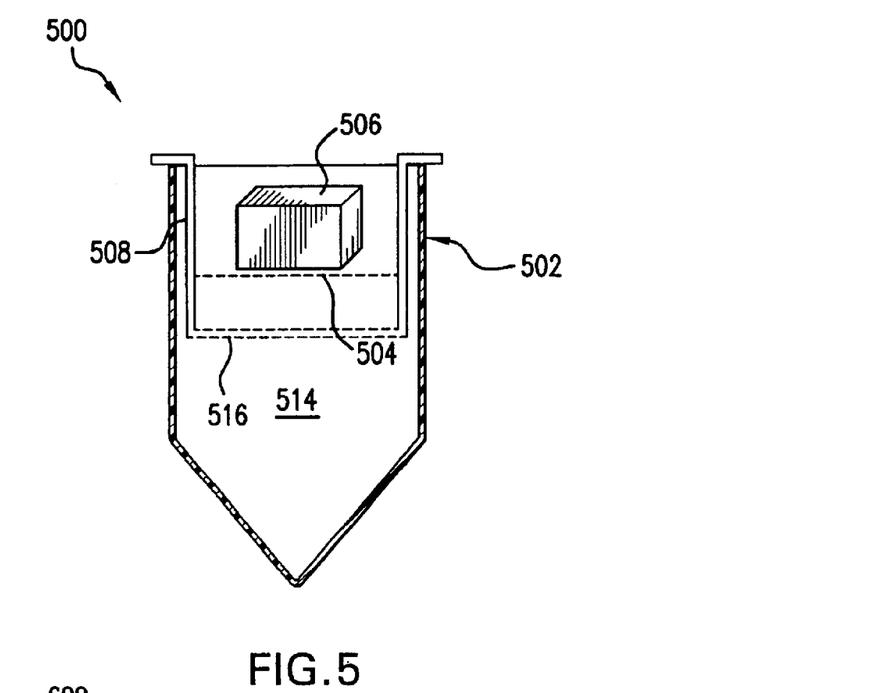
FIG. 5 shows an alternative embodiment of a nested gel mincing tube, including a mesh material bottom and a treating membrane.

FIG. 5 shows an embodiment of a mincing tube apparatus 500 including a nesting tube 508 containing a mesh material 504 and a treating membrane 516. Nesting tube 508 nests within a recovery vessel 502 in the same nesting relationship described previously with reference to FIG. 2. In this embodiment, a mesh material 504 is used to subdivide a gel, such as gel 506, into fragments. Membrane 516 is located in series after mesh material 504. Membrane 516 could be a conditionally porous membrane, which, as stated above, is a membrane having pores of small enough to restrict passage of a solution through the membrane except when a force is applied to the solution. Membrane 516 is also securely attached to nesting tube 508. Mesh material 504 is located in a first portion of nesting tube 508, and membrane 516 is located, spaced apart from mesh material 504, within a second portion of nesting tube 508. The space between mesh material 504 and membrane 516 allows gel 506 to be drawn through mesh material 504 during centrifuging.

During the centrifuging process, gel 506 is divided by and passes through mesh material 504 and accumulates on membrane 516. In one embodiment, membrane 516 contains an immobilized protease, such as trypsin. As the subdivided gel fragments accumulate on membrane 516, the protease will begin to digest proteins that elute from the gel fragments.

Figure 6:
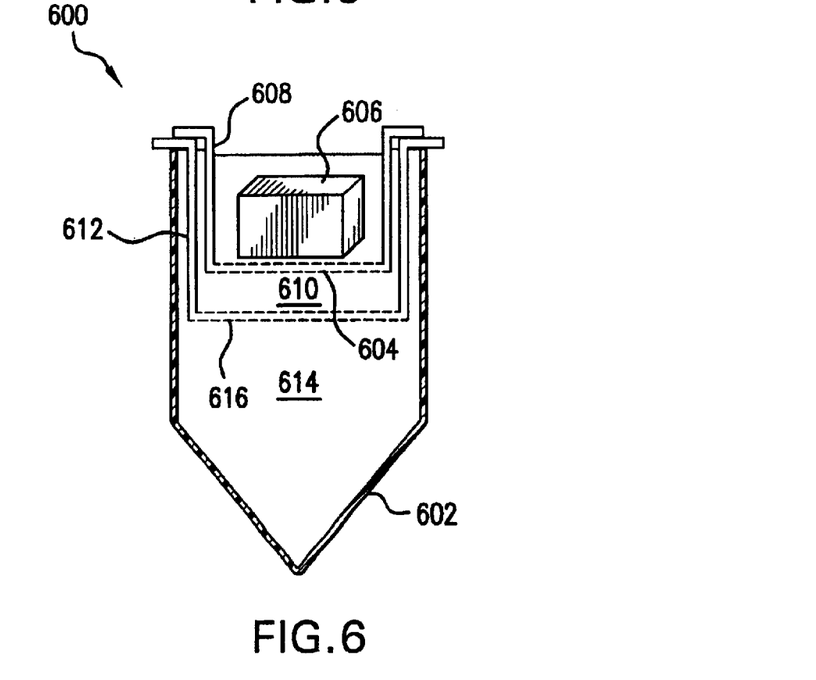
FIG. 6 shows an alternative embodiment of a nested gel mincing tube with a nested treating tube and recovery vessel.

FIG. 6 shows an alternative embodiment of a gel mincing apparatus 600. In this embodiment, gel mincing apparatus 600 includes a mincing tube 608 and a treating tube 612. Mincing tube 608 and treating tube 612 are nesting tubes, and as shown, mincing tube 608 is nested within treating tube 612. A mesh material 604 is secured in mincing tube 608, for subdividing a gel. As described with respect to previous embodiments, mesh material 604 could be located at the top, central area or bottom of mincing tube 608.

A conditionally porous membrane 616 is secured in treating tube 612, for treating a subdivided gel or molecules contained within the gel. Thus, when nested, mesh material 604 and membrane 616 are in series. Membrane 616 could be a conditionally porous membrane, and/or may be modified by the attachment of long-chain alkyl groups, ion exchange groups such as tertiary or quaternary amines, short chain carboxylates or sulfonates, chelating groups for metal ion affinity capture, boronic acids for capture of carbohydrates, and similar modifications. Alternatively, membrane 616 may contain or support particles, such as ion exchange or reversed phase capture particles on the membrane.

In the embodiment shown, treating tube 612 has a greater longitudinal length than mincing tube 608. Accordingly, when nested together, a gap 610 is formed between mesh material 604 and membrane 616. Gap 610 preferably is large enough to fully contain a fragmented gel, after a gel is minced by mesh material 604. However, as would be apparent to one skilled in the relevant art, treating tube 612 need not have a greater longitudinal length than treating tube 612. In one embodiment, either mincing tube 608 or treating tube 612 could have steps or ledges formed into the sides, which would serve to limit the distance that mincing tube 608 could be inserted into treating tube 612.

In another embodiment, the profiles of both mincing tube 608 and treating tube 612 are tapered. Thus mincing tube 608 easily nests within treating tube 612. During manufacturing, gap size 610 may be determined by varying the angle of the taper and the size of any ridges, ledges or steps that may be formed into the profiles of mincing tube 608 and treating tube 612.

In another embodiment, a spacer (not shown) could be placed between mincing tube 608 and treating tube 612, either around the exterior or the interior of the tubes, to determine the size of gap 610.

Treating tube 612 is nested within a recovery vessel 602. Recovery vessel 602 could be a centrifugal tube, as described with respect to the previous embodiments. A cavity 614 is formed between membrane 616 of treating tube 612 and an interior surface of recovery vessel 602. Because mincing tube 608 and treating tube 612 are removably nested within each other, and removably nested within recovery vessel 602, one nested tube could be used without the other, or both nested tubes could be used together in series.

In use, a gel 606 is placed on mesh material 604. During centrifuging, gel 606 is fragmented into smaller pieces, which enter gap 610. If membrane 616 is a treating membrane, having long-chain alkyl groups, ion exchange groups such as tertiary or quaternary amines, affinity capture agents (such as antibodies, ligands, substances or other agents that bind proteins), short chain carboxylates or sulfonates, chelating groups for metal ion affinity capture, boronic acids for capture of carbohydrates, or similar modifications thereon, treating of the gel, and the substances in the gel occurs. If membrane 616 is a non-treating membrane, an extraction solution, such as an extraction buffer, is poured into treating tube 612. After treating, centrifuging draws the extraction solution and the elected substances through membrane 616 into cavity 614 of recovery vessel 602.

In one alternate embodiment, one or more additional treating tube are used in series with mincing tube 608 and treating tube 612. Accordingly, a user can use desired treatments on separate membranes to perform a number of treatments in series, without disassembling the apparatus.

In another alternate embodiment, multiple treating tubes are used in series without gel mincer tube 604.

EXAMPLE 1

In one embodiment of the present invention, the trypsin is immobilized onto microscopic glass particles containing carboxylic acid groups like those available from Sigma Chemical Company, St. Louis, Mo., Catalog Number G3910, p. 482 of the 1999 catalog. Glass particles are activated using carbodimide, See S. S. Wong, above, and will bind proteins such as trypsin through the protein's amino groups. These resulting particles of immobilized trypsin are placed on a filter membrane or other similar support that will retain the particles but allow the passage of solution and protein. The immobilized trypsin membrane is placed into the lumen of the tube such that it is below the mesh layer. These layers are placed in series either by mechanically pushing the membrane into the tube such that it is lower than the nesting mechanism, or by fixing the trypsin layer to the nesting tube as described above, with reference to FIG. 5.

When the mesh and the membrane containing the immobilized trypsin particles are placed in series and spun, the gel is subdivided through the mesh and the small bits of gel and solution fall onto the filter holding the immobilized trypsin. This filter may be a conditionally porous membrane such as a molecular weight cutoff membrane sold by Pall Gelman Corp., of Ann Arbor Mich. Proteins eluted from the gel are digested by the trypsin. The resulting peptides and/or proteins are separated from the immobilized trypsin particles and moved through the membrane into a recovery vessel or capture tube by centrifugal force. The amount of centrifugal force required to draw the peptides and proteins through the membrane depends on the permeability, or molecular weight cutoff, of the membrane supporting the immobilized trypsin. If preferred, these multiple reactions of mincing and treating can be run separately by using single function nested tube sets, such as a mincing tube set and a treating tube set.

EXAMPLE 2

In another embodiment, the trypsin is immobilized onto the membrane itself, such as with the carboxylate modified polyvinylidene difluoride membrane described by Bienvenut et al. The treated membrane can be glued or welded into the bottom of the second nesting centrifuge tube and used in the same way as noted above.

One advantage to using immobilized trypsin, is that by immobilizing the trypsin, the enzyme will not digest other trypsin molecules as happens in solution causing the release of trypsin peptides. Trypsin autolysis is a common problem that further complicates the interpretation of mass spectra of the peptides of interest. By this means, in a single spin, the gel can be subdivided by the mesh material, which will greatly shorten the time period required to elute the proteins and cleave them into a pure aliquot of peptides ready for analysis.

The present invention also provides other processing steps for the subdivided gel. For instance, it is also commonplace to desalt peptides before introducing them into the mass spectrometer. One particularly convenient way to do this is by absorption of the peptides onto reversed-phase resins such as C-18 derivatized silica. This technique is used in a commercial product made by Millipore Corporation called the ZIPTIP and in the similar product made by AmiKa of Gaithersburg, Md. The AmiKa product consists of a resin containing C-18 chains that is attached to the sides of pipette tips. The sample is drawn up so that the peptides can bind to the resin and when the fluid is expelled, the salts are washed out. The bound peptides can be washed further with water then eluted with a mixed aqueous, such as an organic solvent for further analysis.

In addition to processing gels to recover peptides for analytical techniques such as spectroscopy (e.g., IR, V, NMR and the like) and mass spectrometry, the present invention can be used to prepare proteins for Edman sequencing, extraction of samples of nucleic acid for sequencing or amplification, or isolation for use in protein—protein, nucleic acid-protein or nucleic acid-nucleic acid interaction studies where intact protein and/or nucleic acid is needed, and other applications, as would be apparent to one skilled in the relevant art.

EXAMPLE 3

In the present invention, a reversed phase layer can be placed beneath the immobilized trypsin so that the peptides are captured as they are produced. For example, a layer of C-18 modified glass particles may be placed on a filter membrane as described above for immobilized trypsin. The particles are available from Phenomenex, Torrance, Calif.

The immobilized C-18 membrane, as with the immobilized trypsin membrane, can be used in series or in a separate reaction from the subdividing mesh material. In fact, numerous varying membranes may be stacked in any number of custom sequences that a researcher may desire. As an example, a first mincing tube containing a mesh for subdivision of the gel can be placed atop a second nesting treating tube containing immobilized trypsin on a membrane. The sample is first centrifuged at a force sufficient to drive the gel through the mesh and subdivide it but not with a force sufficient to drive the solution through the membrane which holds the trypsin in place. Next, the subdivided gel would be allowed to incubate on the trypsin membrane for time sufficient to allow the protein to be digested. Techniques and incubation times for trypsin digestion of protein are well known in the art.

The tube is then spun to force the peptides and fluid through the conditionally porous membrane holding the trypsin and onto a second conditionally porous membrane filter on which C-18 glass particles are trapped. As the fluid flows through this filter, peptides are captured by the C-18 while the salt solution flows through to the tube bottom or into a separate recovery vessel. The fluids are forced through the column of mesh and membranes having immobilized phases by centrifugal force. A fresh recovery vessel can be placed below the column and the peptides can be eluted into it by applying an elution solvent or buffer of appropriate strength to the top of the column and centrifuging it a second time.

Yet another embodiment uses a nested set of treatment and purification techniques with immobilized antibodies to capture and remove from an analyte sample proteins that are not of interest. For example, it is quite common that after gel separation of proteins one finds that certain high abundance "housekeeping" proteins existing in substantial quantities, migrate in the gel to the same location as low abundance proteins of interest. The high abundance proteins mask the low abundance proteins and make their identification or sequencing difficult. One way to solve this problem is to remove the high abundance proteins, which are generally well known and easily isolated, by binding them selectively with monoclonal antibodies or with polyclonal antibodies raised against them. Methods for the preparation of antibodies are well known in the art.

Although Example 3 describes the use of a membrane having C-18 particles for capturing proteins and peptides for desalting, a membrane having attached alkyl chains shorter than or longer than 18 carbons (e.g., C6, C8, C10, C12, C20, etc.) could be successfully used with the invention. Membranes to which long alkyl chains may be attached are manufactured by Pall Gelman Corp. of Ann Arbor, Mich. Restek Corp. of Bellefonte, Pa. sells extraction disks having alkyl chains of either C-8 or C-18 bound to glass fibers. (C18 disk, 47 mm, Cat. #24004; C8 disk, 47 mm, Cat. #24048). These could also be used as capture media.

In addition to using a membrane or particle coated with an alkyl chain to capture peptides, one might use ion exchange resin particles or, alternatively, membranes modified to have ion exchange properties-derivatized with ionizable groups. Such ion exchangers might be very effective, for example, to capture nucleic acids or certain highly ionic peptides or proteins.

EXAMPLE 4

In this example, antibodies are immobilized on activated glass or other similar substrate in the same way as the trypsin described above. Particles with attached antibodies are placed atop a filter membrane or other similar support with pores sufficient to retain the particles, or the antibodies are immobilized to the membrane itself or to a material, which will not penetrate the filter membrane such as glass fiber. The membrane is then secured across the opening of the tube as previously described. When protein or similar mixtures are placed atop the membrane and the whole assembly centrifuged, the component parts of the mixture capable of binding to the immobilized antibodies are captured and retained above the filter membrane. The filtrate is thus depleted of high abundance proteins, thus allowing the lower abundance proteins to be examined in further analytical procedures.

Particularly useful in this embodiment is a filter membrane that does not readily admit passage of the solutions until subjected to centrifugal force, or, a conditionally porous membrane. Such a membrane could be a polycarbonate membrane that is commercially available from Poretics Corporation of Livermore, Calif.

EXAMPLE 5

The invention can be used and adapted for use with standard processing techniques, such as dehydration and rehydration recovery techniques. One example, using the invention in an In-Gel Tryptic Digest Protocol is described below. This protocol could be varied, as would be apparent to one skilled in the relevant art. The steps are as follows:

1. Excise a desired band from a gel using a clean scalpel or similar excision tool;
2. Place the gel in a nested tube on top of a mesh material;
3. Spin the tube at 10,000 rpm to mince the gel and draw the subdivided gel fragments into a second nested receptacle containing a conditionally porous membrane;

4. Add 250 μL of 50% H$_2$O/50% acetonitrile wash to the minced gel and wash for 5 minutes;
5. Remove the acetonitrile wash by centrifuging the solution through the membrane;
6. Add 250 μL 50% acetonitrile/50 mM NH$_4$HCO$_3$ solution and wash for 30 minutes at room temp, agitation may be helpful;
7. Remove the acetonitrile/NH$_4$HCO$_3$ solution wash by centrifuging;
8. Add 250 μL 50% acetonitrile/10 mM NH$_4$HCO$_3$ and wash for 30 minutes at room temperature;
9. Spin to remove the acetonitrile/NH$_4$HCO$_3$ solution and discard the solutions;
10. Speedvac the minced gel fragments to complete dryness;
11. Add 0.1 μg modified trypsin (Promega) per 15 mm$^3$ of gel in 15 μL of 10 mM NH$_4$HCO$_3$;
12. Let stand for 5–10 minutes to allow enzyme/buffer solution to absorb into the gel;
13. Add an additional 20 μL of 10 mM NH$_4$HCO$_3$ buffer without any additional enzyme;
14. Verify that all the minced gel fragments are covered with the buffer, and if not, increase the buffer volume to cover all the gel fragments;
15. Incubate at 37° C. for 24 hours;
16. Centrifuge and collect supernatant;
17. Perform a second extraction using 200 μL of 60% acetonitrile in water containing 0.1% TFA, and shaking at room temperature for 60 minutes;
18. Centrifuge to collect the extract solution from the receiver tube;
19. Generally two extracts are all that is need for protein identification by MALDI-TOF MS, however, for quantitation purposes, a third extraction may be necessary and thus steps 17 and 18 would be repeated;
20. Speedvac the extract solution down to 5–10 μL; and
21. For MALDI-MS mix 1 μL of the extract with 1 μL of internal standards (i.e. containing 100 fmol of bradykinin) and 1 μL of α-cyano-4-hydroxy-trans-cinnamic acid.

EXAMPLE 6

An additional sample protocol using the present invention is described below.
1. Excise both a desired gel band and a blank gel piece of approximately the same size with an ethanol rinsed scalpel;
2. Place each sliced gel on top of a mesh material in individual mincer tubes respectively;
3. Spin tubes at 10,000 rpm to mince the gels and pass gel fragments onto membranes;
4. Dehydrate the minced fragments in 200 μL MeOH for 5 minutes, then rehydrate the fragments with 200 μL 30%MeOH/H$_2$O, shaking the tube for 5 minutes;
5. Wash gel fragments in 200 μL water for 10 minutes, two times;
6. Wash gels fragments with 100 mM ammonium bicarbonate/30% acetonitrile for 10 minutes at a time, until colorless (minimum 3 washes). One final wash in water may be done to reduce buffer concentration and speed the drying process;
7. Dry the gel fragments in a speedvac;
8. Rehydrate the gel fragments in 2 mM Tris-HCl/300 ng modified sequence grade Trypsin or 25 mM ammonium bicarbonate/300 ng modified sequence grade Trypsin, taking care to provide sufficient volume to completely cover the gel fragments in case they swell;
9. Carefully vortex to mix the gel fragments and rehydration solution and incubate at 37° C. for at least 8 hours;
10. Centrifuge the tube to pass the supernatant to the bottom of the tube;
11. Extract fragments using 50% acetonitrile/0.1% TFA for 10 minutes at room temp;
12. Centrifuge to add extract solution to the supernatant from the digestion;
13. Speedvac the extract solution to reduce the solution volume to 10 μL; and
14. Apply 1 μL of the extract with 2 μL of the appropriate MALDI matrix for MS analysis.

The protocol may be varied in many ways, as would be apparent to one skilled in the relevant art. Furthermore, additional or optional treatments or steps may be used. For instance, in one optional treatment, the centrifuge tube may contain a few milligrams of reverse phase resin. After collecting the supernatant and first extract as described in step 9–11, the volume of the acetonitrile solution may be reduced to allow binding of the digested peptides to the resin. The resin then, may be washed several times with 25 mM ammonium bicarbonate. Peptides may be removed from the resin by mixing the resin with 80% acetonitrile/25 mM ammonium bicarbonate. The eluted peptides are transferred to a clean microfuge tube and evaporated to 10 μL using a speedvac.

EXAMPLE 7

An additional sample protocol using the present invention is described below.
1. Excise a desired band from a gel using a clean scalpel or similar excision tool;
2. Place the gel slice in a nested tube on top of a mesh material;
3. Spin tube at 10,000 rpm to mince gel and draw minced gel fragments onto a membrane when using an Eppendorf 5415C centrifuge;
4. Remove first nested tube containing the mincing mesh;
5. Wash gel by adding 100 μL of ultra pure water to cover the minced gel pieces. If pieces are not covered, add enough water to completely cover the fragments;
6. Allow the gel to incubate for 15 minutes, then spin the tube to pass the water through the membrane and into the collection tube;
7. Repeat steps 5 and 6;
8. Repeat steps 5 and 6 using 25 mM ammonium bicarbonate instead of ultrapure water;
9. Transfer the nested tube containing the membrane and minced gel pieces into a clean 1.5 mL Eppendorf microfuge tube and place into a speedvac;
10. Speedvac the gel fragments to complete dryness;
11. Add 0.1 μg of modified trypsin (Promega) per 15 mm$^3$ of gel in 25 μL of 10 mM ammonium bicarbonate;
12. Let stand for 5–10 minutes to allow the enzyme/buffer solution to absorb into the gel;
13. Add an additional 25–50 μL of ammonium bicarbonate without enzyme to completely cover all of the gel fragments;

14. Incubate at 37° C. overnight or approximately 16 hours;
15. Centrifuge and collect the supernatant;
16. Remove the nested tube containing the membrane and gel fragments from the Eppendorf collection tube and reduce the volume to 5–10 µL using a speedvac (the first extract typically contains enough peptide fragments for protein identification by MALDI-TOF Mass spectrometry); and
17. Apply the collected solution containing peptides fragments, along with the appropriate MALDI matrix, to the stage plate and an internal standard, if desired.

EXAMPLE 8

In one aspect of the invention, an Eppendorf 5415C centrifuge is used to mince a gel. Test results are displayed in the table below.

TABLE 1

|  | 4% TG | | 8% TG | | 10% TG | | 10% BT | | 12% BT | | 20% TG | |
|---|---|---|---|---|---|---|---|---|---|---|---|---|
| RCF | A | B | A | B | A | B | A | B | A | B | A | B |
| 2040 × g | − | + | − | − | | | | | | | | |
| 4000 × g | + | + | − | + | | | | | | | | |
| 8160 × g | | | + | + | +/− | + | +/− | +/− | | | | |
| 11,750 × g | | | | | + | + | + | + | +/− | + | +/− | + |
| 16,000 × g | | | | | | | | | + | + | +/− | |

The gels used in the test and the symbol definitions are set forth below.

4%TG—4% acrylamide crosslinked with 2.5% bisacrylamide

8%TG—8% acrylamide crosslinked with 2.5% bisacrylamide

10%TG—10% acrylamide crosslinked with 2.5% bisacrylamide

10% BT—10% acrylamide crosslinked with 2.5% bisacrylamide

12% BT—12% acrylamide crosslinked with 2.5% bisacrylamide

20%TG—20% acrylamide crosslinked with 2.5% bisacrylamide

"A" represents a mesh material having openings with a width of 0.0145 inch, and a wire diameter 0.0055 inch.

"B" represents a mesh material having openings with a width of 0.0267 inch, and a wire diameter 0.0065 inch.

"+" represents gel completely drawn through the mesh.

"−" represents gel not drawn through the mesh.

"+/−" represents some of the gel drawn through the mesh and some of the gel left on the mesh.

In specific embodiments, centrifuging to facilitate passage of the semisolid material through the mesh, thereby subdividing the semisolid material into fragments, can be completed at Relative Centrifugal Force (RCF) in the ranges of about 1,000×g to 26,000×g, about 1,000×g to 24,000×g, about 1,000×g to 20,000×g, about 1,000×g to 16,000×g, about 1,000×g to 12,000×g, about 1,000×g to 8,000×g, about 1,000×g to 6,000×g, about 1,000×g to 4,000×g, about 1,000×g to 2,000×g, about 4,000×g to 24,000×g, about 4,000×g to 20,000×g, about 4,000×g to 16,000×g, about 4,000×g to 12,000×g, about 4,000×g to 8,000×g, about 4,000×g to 6,000×g, about 8,000×g to 24,000×g, about 8,000×g to 20,000×g, about 8,000×g to 16,000×g, about 8,000×g to 12,000×g about 8,000×g to 10,000×g, about 10,000×g to 24,000×g, about 10,000×g to 20,000×g, about 10,000×g to 16,000×g, about 10,000×g to 12,000×g, about 12,000×g to 24,000×g, about 12,000×g to 16,000×g, about 12,000×g to 14,000×g, about 16,000×g to 24,000×g, about 16,000×g to 20,000×g and about 20,000×g to 24,000×g.

The use of centrifugal force to drive the solutions through the various layers, affixes the layers together. Thus, a pressure seal between the layers is optional. Each tube segment is an interchangeable module so that the user can readily assemble a nested tube set custom designed for his particular analyte processing needs.

For example, one part of the nested set can provide the sieve or mesh material to subdivide the gel. Another part can provide the immobilized trypsin held in place by a porous membrane or conditionlly porous membrane or immobilized on a membrane itself. Another part can provide the reversed phase capture material, either held in place by a membrane or by using membrane derived so as to bind proteins by hydrophobic interactions. Another part can provide the immobilized antibody to capture a high abundance protein. Several types of such immobilized antibodies (or portions thereof, e.g., Fc fragments, Fab or Fab'$_2$ fragments, H or L chains, or combinations thereof) might be provided either as separate segments for nesting or combined in a single segment. The last segment can be a receptacle or recovery vessel for fluid driven through the column by centrifugal force. Such a segment can be removed to discard fluids and a fresh one put in place for the elution of the peptides or proteins of interest from the column. Moreover, segments of a nested tube set can be removed between steps.

Specifically, if the objective is to capture peptides on a reversed phase packing after the gel is subdivided by the mesh and digested with trypsin, the mesh and trypsin segments of this nested set of tubes might be removed and discarded or cleaned for reuse before the peptides are eluted from the reversed phase with a mixed solvent system.

As a further example of the versatility of this invention, tubes may be inverted and placed into larger filter-containing tubes for subsequent processing steps. For example, following subdivision of gel and extraction of the protein, if some of the more abundant proteins need to be removed, a second tube containing a filter and antibodies immobilized on membrane can be used. The second tube is placed on the top in way that when the tubes are inverted and spun briefly by the centrifuge, the sample containing solution passes through the filter and comes in contact with the immobilized antibodies. The protein can be kept in contact with the antibodies as long as needed. This same concept of inversion can be extended to the other sample processing steps such as digestion, purification and so on.

The system for mincing and treating gel materials is highly flexible since a wide variety of processes can be conducted in series in the nested tubes and different procedures can be selected by using different prepared tubes. For example, one tube might contain trypsin while another might contain papain, and the user can select whichever tube best meets the needs of the process to be conducted. In one embodiment, these nested tubes are nested microtiter plates, wherein an array of nested tubes align with tubes of a microtiter plate. A microtiter plate links together, or has formed therein, an array of tubes with closed bottoms. A mincing tube or a treating tube could be a set of tubes arrayed in an 8×12 or 16×24 format, or other format, with centers compatible with standard microtiter plates so that the tube array can be mated with conventional microtiter plates as receiver plates. Since centrifuge equipment is readily available from Fisher (Marathon 21000 and 21000R centrifuges, Fisher Scientific, Pittsburgh, Pa.), Brinkmann (Eppendorf 5804 and 5810 centrifuges, Brinkmann Instruments Inc., Westbury, N.Y.) and others, that allow an entire microtiter plate of 96, 384 or more wells to be spun simultaneously, the above-described nested tube set can be provided in the form of nested microtiter plates. This will allow easy simultaneous processing of a multiplicity of samples without having to handle individual tube segments, making this invention especially useful in high throughput analysis.

The invention further includes methods for isolating and/or purifying molecules such as macromolecules, peptides, oligonucleotides, and carbohydrates. These methods comprise (a) placing a gel subportion upon the mesh material of a mincing tube described above, (b) centrifuging the mincing tube, the mesh, and the gel subportion to facilitate passage of the gel subportion through the mesh so as to divide the gel subportion into fragments, and (c) extracting the gel subportion fragments with an extraction solution. Optionally, the molecules extracted by the extraction solution, and present therein, may be concentrated by, for example, precipitation or evaporation of extraction solution solvent(s). Typically, the gel subportion fragments will be separated from the extraction solution prior to analysis by mass spectroscopy.

The invention also includes methods for isolating and/or purifying molecules such as macromolecules, peptides, oligonucleotides, and carbohydrates. These methods comprise (a) separating one or more molecules by gel electrophoresis, (b) sectioning the resulting gel to obtain a subportion thereof which contains one or more molecules of interest, (c) placing the gel subportion upon the mesh material of a mincing tube described above, (d) centrifuging the mincing tube, the mesh, and the gel subportion to facilitate passage of the gel subportion through the mesh so as to divide the gel subportion into fragments, and (e) extracting the gel subportion fragments with an extraction solution.

As one skilled in the art would recognize, extraction solutions used in methods of the invention may be either aqueous or non-aqueous.

Further, the pH of extraction solutions used in methods of the invention may be basic, acidic, or neutral. When basic extraction solutions are used, these solutions may have a pH which is about 7.5, about 8.0, about 8.5, about 9.0, about 9.5, about 10.0, about 10.5, about 11.0, about 11.5, about 12.0, about 12.5, about 13.0, about 13.5, or about 14.0. When acidic extraction solutions are used, these solutions may have a pH which is about 6.5, about 6.0, about 5.5, about 5.0, about 4.5, about 4.0, about 3.5, about 3.0, about 2.5, about 2.0, about 1.5, about 1.0, or about 0.5. Further, the extraction solution may have a pH in any of the following ranges: from about pH 1.0 to about pH 5.0, from about pH 2.0 to about pH 6.0, from about pH 3.0 to about pH 7.0, from about pH 4.0 to about pH 8.0, from about pH 5.0 to about pH 9.0, from about pH 6.0 to about pH 10.0, from about pH 7.0 to about pH 11.0, from about pH 8.0 to about pH 12.0, and from about pH 9.0 to about pH 13.0.

Extraction solutions used in methods of the invention may contain one or more agents which facilitate and/or inhibit the degradation of particular classes of molecules. For example, when methods of the invention are designed for the purification and/or isolation of proteins, the extraction solution may contain protease inhibitors (e.g., PMSF) and one or more ribonucleases which will facilitate the digestion of RNA. Similarly, when methods of the invention are designed for the purification and/or isolation of DNA, the extraction solution may be substantially free of deoxyribonucleases but may contain one or more ribonucleases.

The invention further includes methods for identifying molecules such as macromolecules, peptides, oligonucleotides, and carbohydrates. These methods comprise (a) placing a gel subportion upon the mesh material of a mincing tube described above, (b) centrifuging the mincing tube, the mesh, and the gel subportion to facilitate passage of the gel subportion through the mesh so as to divide the gel subportion into fragments, (c) extracting the molecules from the gel subportion fragments with an extraction solution, and (d) performing mass spectroscopy (e.g., tandem mass spectroscopy, matrix-assisted laser desorption/ionization mass spectrometry (MALDI-MS), inductively coupled plasma mass spectroscopy (ICP-MS), Fourier transform ion cyclotron resonance mass spectroscopy, (FTICR-MS), electrospray mass spectrometry (ES-MS), etc.) on the extraction solution to identify molecules present. Typically, the gel subportion fragments will be separated from the extraction solution prior to analysis by mass spectroscopy.

The invention also includes methods for identifying molecules such as macromolecules, peptides, oligonucleotides, and carbohydrates. These methods comprise (a) separating one or more molecules by gel electrophoresis, (b) sectioning the resulting gel to obtain a subportion thereof which contains one or more molecules of interest, (c) placing the gel subportion upon the mesh material of a mincing tube described above, (d) centrifuging the mincing tube, the mesh, and the gel subportion to facilitate passage of the gel subportion through the mesh so as to divide the gel subportion into fragments, (e) extracting the molecules from the gel subportion fragments with an extraction solution, and (f) performing mass spectroscopy (or other analytical techniques, such as those described elsewhere herein) on the extraction solution to identify molecules present.

The invention further includes methods for sequencing molecules such as macromolecules, peptides, oligonucleotides, and carbohydrates. These methods comprise (a) placing a gel subportion upon the mesh material of a mincing tube described above, (b) centrifuging the mincing tube, the mesh, and the gel subportion to facilitate passage of the gel subportion through the mesh so as to divide the gel subportion into fragments, (c) extracting the molecules from the gel subportion fragments with an extraction solution, and (d) performing mass spectroscopy (e.g., tandem mass spectroscopy, MALDI-MS, ES-MS, FTICR-MS, ICP-MS, etc.) on the extraction solution to identify molecules present. As noted above, typically, the gel subportion fragments will be separated from the extraction solution prior to analysis by mass spectroscopy.

The invention also includes methods for sequencing molecules such as macromolecules, peptides, oligonucleotides, and carbohydrates. These methods comprise (a) separating one or more molecules by gel electrophoresis, (b) sectioning the resulting gel to obtain a subportion thereof which contains one or more molecules of interest, (c) placing the gel subportion upon the mesh material of a mincing tube described above, (d) centrifuging the mincing tube, the mesh, and the gel subportion to facilitate passage of the gel subportion through the mesh so as to divide the gel subportion into fragments, (e) extracting the molecules from the gel subportion fragments with an extraction solution, and (f) performing mass spectroscopy (e.g., tandem mass spectroscopy, MALDI-MS, ES-MS, FTICR-MS, ICP-MS, etc.) on the extraction solution to identify molecules present.

Methods for performing mass spectroscopy are described in U.S. Pat. Nos. 6,238,871, 5,955,729, 5,854,486, 5,716,825, 5,705,813, the entire disclosures of which are incorporated herein by reference. In particular, Koster et al., U.S. Pat. No. 6,238,871, describe methods for sequencing nucleic acids using mass spectrometry (e.g., MALDI-MS and ES-MS).

It should be understood, that the described methods may be used to isolate proteins, peptides, nucleic acids and other substances, including all types of macromolecules.

In one aspect of the invention, a kit for mincing and treating a gel is provided. Kits serve to expedite the performance of, for example, methods of the invention by providing multiple components and reagents packaged together. Further, reagents of these kits can be supplied in pre-measured units so as to increase precision and reliability of the methods. The kit may comprise a carrier being compartmentalized to receive one or more components of the kit. Kits of the invention for mincing a gel and extracting an analyte from a gel generally comprising a carton such as a box, one or more containers such as boxes, tubes, ampules, jars, bags, plates and the like, a mincing tube and any combination of one or more of the below listed items.

The kit of the invention may comprise a receiving vessel or a treating tube containing a conditionally porous membrane, as described above with reference to the Figures.

The kit may comprise one or more solutions, or a material to prepare one or more solutions, to treat a gel, such as, for example, a trypsin enzyme in a compatible salt solution or, alternatively, a packaged dry enzyme. The solution may include an aqueous, nonaqueous or mixed solvent for eluting captured proteins or peptides from a conditionally porous membrane. Further, the solution could be a solvent, a buffer solution, or a solution containing a reagent, such as trypsin, a long-chain alkyl group, an ion exchange group, a short chain carboxylate or sulfonate, a chelating group or a boronic acid. The kit may include other solutions including aqueous, nonaqueous or mixed solvents to be used in eluting captured proteins or peptides from conditionally porous membranes which have been modified to treat or extract components from the gel.

The kit may include one or more spare membranes or spare mesh material, or mesh material having different hole sizes to enable a user to custom fragment the gel. The kit may contain printed instructions for use.

The kit may comprise one or more treated or untreated membranes for the selective removal of components from the gel which may interfere or compromise subsequent analytical procedures. The membranes may be treated with long-chain alkyl groups, ion exchange groups such as tertiary or quaternary amines, short chain carboxylates or sulfonates, chelating groups for metal ion affinity capture or boronic acid. The kit may include particles, such as ion exchange or reversed phase capture particles on the membrane.

The kit of the invention may further comprise one or more items including a gel or a gel electrophoresis apparatus, a pipette or a spatula.

While the invention has been particularly shown and described with reference to preferred embodiments thereof, it will be understood by those skilled in the art that various changes in form and detail may be made therein without departing from the spirit and scope of the invention.

All publications, articles and patents referred to herein, including U.S. Provisional Application No. 60/218,821, are incorporated by reference in their entirety.

We claim:

1. A method for subdividing gel material using a tube or container having a mesh disposed therein, the method comprising:
    (a) contacting gel material with the mesh of the tube or container; and
    (b) centrifuging the tube or container sufficient to cause gel material to pass through the mesh, thereby subdividing gel material into fragments.

2. The method of claim 1, further comprising:
    (c) introducing a solution to the subdivided gel material; and
    (b) eluting an analyte from the subdivided gel material.

3. The method of claim 2, wherein the analyte comprises at least one or more components selected from the group consisting of a protein, a peptide, a nucleic acid and a carbohydrate.

4. A method for subdividing gel material using a tube or container having a mesh disposed therein and a recovery vessel having a conditionally porous material disposed therein, the method comprising:
    (a) contacting gel material with the mesh of the tube or container;
    (b) centrifuging the tube or container sufficient to cause gel material to pass through the mesh, thereby dividing gel material into fragments; and
    (c) causing an analyte recovered from the subdivided gel material to contact the conditionally porous material.

5. The method of claim 4, wherein the conditionally porous material comprises one or more components selected from the group consisting of a long-chain alkyl group, an ion exchange group, an antibody, a short chain carboxylate or sulfonate, a chelating group and a boronic acid.

6. The method of claim 4, wherein the conditionally porous material comprises a polyvinylidene difluoride membrane, a nylon membrane, a nitrocellulose membrane and/or a glass fiber membrane.

7. A method for the treatment of a gel material using a tube or container having a mesh disposed therein and a conditionally porous material disposed therein in series, comprising:
    (a) contacting the gel material with the mesh of the tube or container; and
    (b) centrifuging the tube or container sufficient to cause gel material to pass through the mesh thereby subdividing the gel material into fragments, and sufficient to cause at least a portion of the subdivided gel material to pass through the conditionally porous material.

8. The method of claim 7, wherein the conditionally porous material comprises a polyvinylidene difluoride membrane, a nylon membrane, a nitrocellulose membrane and/or a glass fiber membrane.

9. The method of claim 7, wherein the tube or container comprises an array of tubes for aligning and mating with a microtiter plate.

10. The method of claim 7, wherein the mesh is disposed at a first end of the tube or container and the conditionally porous material is disposed at a second end of the tube or container.

11. The method of claim 7, wherein reactants are disposed on the conditionally porous material, and wherein the reactants comprise one or more components selected from the groups consisting of a long-chain alkyl group, an ion exchange group, an antibody, a short-chain carboxylate or sulfonate, a chelating group and a boronic acid.

12. A method for the division of gel material using a tube or container having a mesh disposed therein and a recovery vessel, wherein the tube or container is nested in the recovery vessel, the method comprising:
   (a) contacting gel material with the mesh of the tube or container; and
   (b) centrifuging the tube or container and the recovery vessel sufficient to cause gel material to pass through the mesh, thereby subdividing gel material into fragments, wherein the subdivided gel material is captured by the recovery vessel.

13. The method of claim 12, wherein the tube or container comprises an array of tubes for aligning and mating with a microtiter plate.

14. A method for the division of gel material using a first tube or container having a mesh disposed therein, a recovery vessel, and a second tube or container nested in series after the first tube or container and before the recovery vessel, wherein the second tube or container includes a conditionally porous material disposed therein, and the conditionally porous material is in series with the mesh, the method comprising:
   (a) contacting gel material with the mesh of the first tube or container; and
   (b) centrifuging the first tube or container, the recovery vessel and the second tube or container sufficient to cause gel material to pass through the mesh, thereby subdividing gel material into fragments, and sufficient to cause at least a portion of the subdivided gel material to pass through the conditionally porous material, wherein the portion of the subdivided gel material is captured by the recovery vessel.

15. The method of claim 14, wherein the conditionally porous material comprises a polyvinylidene difluoride membrane, a nylon membrane, a nitrocellulose membrane and/or a glass fiber membrane.

16. The method of claim 14, wherein a reagent is attached to the conditionally porous material.

17. The method of claim 16, wherein the attached reagent comprises one or more of the group consisting of: a long-chain alkyl group, an ion exchange group, an antibody, strepavidin, a short chain carboxylate or sulfonate, a chelating group and a boronic acid.

18. The method of claim 16, wherein the attached reagent comprises one or more of the group consisting of: immobilized trypsin, immobilized chymotrypsin, immobilized pepsin, immobilized papain, immobilized carbon chains and immobilized antibodies.

19. A method for subdividing gel material using a tube or container having a mesh disposed therein, said mesh having a hole size between 0.01 $mm^2$ to 9.0 $mm^2$, the method comprising:
   (a) contacting gel material with the mesh of the tube or container; and
   (b) centrifuging the tube or container sufficient to cause gel material to pass through the mesh, thereby subdividing gel material.

* * * * *